(12) United States Patent
Beattie et al.

(10) Patent No.: US 11,344,523 B2
(45) Date of Patent: May 31, 2022

(54) COMPOSITION FOR USE IN TREATING ROTAVIRUS INFECTION

(71) Applicant: Devenish Nutrition Limited, Belfast (GB)

(72) Inventors: Violet Emma Beattie, Tyrone (GB); Gordon Moore Allan, Belfast (GB); Andrena Millar, Dundonald (GB); John Paul McKillen, Belfast (GB)

(73) Assignee: Devenish Nutrition Limited, Belfast (GB)

(*) Notice: Subject to any disclaimer, the term of this patent is extended or adjusted under 35 U.S.C. 154(b) by 0 days.

(21) Appl. No.: 16/827,133

(22) Filed: Mar. 23, 2020

(65) Prior Publication Data
US 2020/0222350 A1 Jul. 16, 2020

Related U.S. Application Data

(62) Division of application No. 16/314,214, filed as application No. PCT/EP2017/066396 on Jun. 30, 2017, now abandoned.

(30) Foreign Application Priority Data

Jun. 30, 2016 (GB) .................................. 1611365.6

(51) Int. Cl.
| | | |
|---|---|---|
| *A61K 31/20* | (2006.01) | |
| *A61P 31/14* | (2006.01) | |
| *A61K 31/19* | (2006.01) | |
| *A61P 31/20* | (2006.01) | |
| *A61P 31/22* | (2006.01) | |

(52) U.S. Cl.
CPC .............. *A61K 31/20* (2013.01); *A61K 31/19* (2013.01); *A61P 31/14* (2018.01); *A61P 31/20* (2018.01); *A61P 31/22* (2018.01)

(58) Field of Classification Search
CPC ........ A61K 31/14; A61K 31/19; A61K 31/20; A61P 31/14; A61P 31/20; A61P 31/22
See application file for complete search history.

(56) References Cited

U.S. PATENT DOCUMENTS

| | | | |
|---|---|---|---|
| 9,023,797 B2 | 5/2015 | Lebing et al. | |
| 2002/0173545 A1 | 11/2002 | Gutzman | |
| 2010/0317734 A1 | 12/2010 | Folar et al. | |
| 2011/0300229 A1* | 12/2011 | Buchan .................. | A61K 35/20 424/535 |

FOREIGN PATENT DOCUMENTS

| | | | |
|---|---|---|---|
| CN | 105 012 286 A | 11/2015 | |
| EP | 1 123 701 A1 | 8/2001 | |
| EP | 2 695 620 A1 | 2/2014 | |
| WO | WO-0168085 A1 * | 9/2001 | ........... A61K 35/741 |
| WO | WO-2011134802 A1 * | 11/2011 | ............... A61P 21/06 |
| WO | WO-2014167554 A2 * | 10/2014 | ........... A61K 8/4926 |

OTHER PUBLICATIONS

Vincent Racaniello, "How many viruses on Earth?", Virology blog: About viruses and viral disease, published online Sep. 6, 2013, pp. 1-6 (Year: 2013).*
Woolhouse et. al., Phil. Trans. of Royal Soc. B, 2012, The Royal Soc., vol. 367, pp. 2864-2871 (Year: 2012).*
Ismail-Cassim et. al., J. Gen. Virology, 1990, vol. 71, pp. 2283-2289 (Year: 1990).*
U.S. Appl. No. 16/314,214, filed Dec. 28, 2018.
Curtis et al. (1966) "Infectious bovine rhinotracheitis - clinical, pathological, and virological aspects," Can Vet J. 7(8):161-168.
Dulac et al. (1989) "Porcine circovirus antigens in PK-15 cell line (Atcc CCL-33) and evidence of antibodies to circovirus in Canadian pigs," Can. J. Vet. Res. 53(4):431-433.
Hueffer et al. (2003) "Parvovirus host range, cell tropism and evolution," Curr Opin Microbial. 6(4):392-398. Abstract Only.
Kaku et al. (2001) "Genetic reclassification of porcine enteroviruses," J. Gen. Viral 82(2): 417-424.
Meehan et al. (1998) "Characterization of novel circovirus DNAs associated with wasting syndromes in pigs," J. Gen. Viral. 79(9): 2171-2179.
Nagy et al. (2001) "The complete nucleotide sequence of porcine adenovirus serotype 5," J. Gen. Viral. 82(3): 525-529.
Search Report and Written Opinion, dated Oct. 17, 2017, corresponding to International Application No. PCT/EP2017/066396 (filed Jun. 30, 2017) of which the parent application U.S. Appl. No. 16/314,214 is a US National Stage 9 pages.
GenBank accession No. KU 198480. Bovine herpesvirus 1 strain Cooper, complete genome. Submitted Nov. 26, 2015. Latest version Mar. 9, 2016.
GenBank accession No. NC_001718. Porcine parvovirus, complete genome. Submitted Aug. 1, 2000. Latest version Aug. 13, 2018.
GenBank accession No. AF055392. Porcine circovirus 2 from Canada, complete genome. Submitted Mar. 26, 1998. Latest version Mar. 19, 2009.
GenBank accession No. AF289262. Porcine adenovirus 5, complete genome. Submitted Jul. 24, 2000. Latest version Mar. 26, 2001.

* cited by examiner

*Primary Examiner* — Sarah Pihonak
(74) *Attorney, Agent, or Firm* — Leydig, Voit & Mayer, Ltd.

(57) ABSTRACT

The present invention relates to a composition comprising at least one carboxylic acid selected from butanoic acid, hexanoic acid, octanoic acid, decanoic acid, and dodecanoic acid for use in treating a viral infection. Also disclosed is use of a composition comprising at least one carboxylic acid selected from butanoic acid, hexanoic acid, octanoic acid, decanoic acid, and dodecanoic acid in the manufacture of a medicament for treating a viral infection; and a method for treating a viral infection in a subject.

13 Claims, No Drawings

COMPOSITION FOR USE IN TREATING ROTAVIRUS INFECTION

CROSS REFERENCE TO RELATED APPLICATIONS

This application is a divisional application of U.S. Ser. No. 16/314,214, filed Dec. 28, 2018, which is a U.S. National Stage Application under 35 U.S.C. § 371 of International Application No. PCT/EP2017/066396, filed Jun. 30, 2017, which claims the benefit of Great Britain Patent Application No 1611365.6, filed Jun. 30, 2016, each of which is hereby incorporated by reference to the extent not inconsistent herewith.

BACKGROUND TO THE INVENTION

Rotavirus is the most common cause of severe diarrhoea among infants and young children. It is a genus of double-stranded RNA virus in the family Reoviridae. There are seven serogroups of this virus, referred to as A, B, C, D, E, F and G. Rotavirus A, the most common, causes more than 90% of infections in humans. The virus is transmitted by the faecal-oral route. It infects and damages the cells that line the small intestine and causes gastroenteritis (often called "stomach flu").

Worldwide, more than 450,000 children under five years of age, most of who live in developing countries, still die from rotavirus infection each year, and almost two million more become severely ill. In the United States, before initiation of the rotavirus vaccination programme, rotavirus caused about 2.7 million cases of severe gastroenteritis in children, almost 60,000 hospitalisations, and around 37 deaths each year. Public health campaigns to combat rotavirus focus on providing oral rehydration therapy for infected children and vaccination to prevent the disease.

Although rotavirus was discovered in 1973 and accounts for up to 50% of hospitalisations for severe diarrhoea in infants and children, its importance is still not widely known within the public health community, particularly in developing countries.

In addition to its impact on human health, rotavirus also infects animals, and is a pathogen of livestock. Rotaviruses infect the young of many species of animals and are a major cause of diarrhoea in wild and reared animals worldwide. As a pathogen of livestock, notably in young calves, piglets, and foals; rotaviruses cause economic loss to farmers because of costs of treatment associated with high morbidity and mortality rates. These rotaviruses are also a potential reservoir for genetic exchange with human rotaviruses. There is evidence that animal rotaviruses can infect humans, either by direct transmission of the virus or by contributing one or several RNA segments to re-assortments within human strains.

In swine, rotavirus groups A and C predominate and the incubation period is 18-24 hours, after which, depression in appetence and reluctance to move are noted. Vomiting may be seen. A few hours later, profuse diarrhoea develops and, in milk-fed pigs, this is yellow with floccules floating in a whey-like fluid, while in others it may be yellow or dark grey. There is a rapid loss of condition. Inappetence continues for 24-72 hours, after which, appetite returns. Clinical signs regress 4-6 days after infection but loose yellow faeces may persist for 7-14 days. Thirty-three percent of affected young pigs may die in a field outbreak. Weaned pigs may also be affected but, in them, no diarrhoea 40 or only transient diarrhoea (mean duration 3 days) results when rotavirus is demonstrated in the faeces.

Rotavirus is also one of the most common causes of diarrhoea in new-born foals. Outbreaks are common in breeding farm environments. The virus usually affects foals 2-5 months of age. The diarrhoea can last anywhere from 1-9 days and the virus is shed in faeces up to 3 days after return to normal manure. Treatment of foals with rotavirus includes supportive care, fluid therapy and electrolyte replacement. Some foals may require hospitalization.

Although rotavirus vaccines are available for humans, pigs, and foals, each of which are serogroup specific in protection; outbreaks of rotavirus-associated diarrhoea are still common in these species, and require fluid therapy and electrolyte replacement.

SUMMARY OF THE INVENTION

According to a first aspect of the present invention, there is provided a composition comprising at least one carboxylic acid selected from butanoic acid, hexanoic acid, octanoic acid, decanoic acid, and dodecanoic acid.

According to a second aspect of the present invention, there is provided a composition for use in treating a viral infection, the composition comprising at least one carboxylic acid selected from butanoic acid, hexanoic acid, octanoic acid, decanoic acid, and dodecanoic acid.

According to a third aspect of the present invention, there is provided a method for treating a viral infection in a subject, the method comprising the step of administering a composition comprising at least one carboxylic acid selected from butanoic acid, hexanoic acid, octanoic acid, decanoic acid, and dodecanoic acid to the subject.

According to a fourth aspect of the present invention, there is provided use of a composition comprising at least one carboxylic acid selected from butanoic acid, hexanoic acid, octanoic acid, decanoic acid, and dodecanoic acid in the manufacture of a medicament for treating a viral infection.

Optionally, the viral infection is a Group III viral infection. Further optionally, the viral infection is a Reoviridae infection. Still further optionally, the viral infection is a Sedoreovirinae infection. Still further optionally, the viral infection is a rotavirus infection.

Optionally, the viral infection is a human viral infection. Alternatively, the viral infection is a porcine viral infection. Further alternatively, the viral infection is an equine viral infection. Still further alternatively, the viral infection is a bovine viral infection.

Optionally, the subject of the viral infection is a human subject. Alternatively, the subject of the viral infection is porcine subject. Further alternatively, the subject of the viral infection is equine subject.

Still further alternatively, the subject of the viral infection is bovine subject. Still further alternatively, the subject of the viral infection is an avian bovine subject.

By "butanoic acid" is meant a C4 carboxylic acid having the general formula $CH_3CH_2CH_2$—COOH, optionally referred to as butyric acid, 1-propanecarboxylic acid, or propanecarboxylic acid.

By "hexanoic acid" is meant a C6 carboxylic acid having the general formula $CH_3CH_2CH_2CH_2CH_2$—COOH, optionally referred to as caproic acid, or n-Caproic acid.

By "octanoic acid" is meant a C8 carboxylic acid having the general formula $CH_3CH_2CH_2CH_2CH_2CH_2CH_2$—COOH, optionally referred to as caprylic acid.

By "decanoic acid" is meant a C10 carboxylic acid having the general formula $CH_3CH_2CH_2CH_2CH_2CH_2CH_2CH_2CH_2$—COOH, optionally referred to as capric acid, n-Capric acid, n-decanoic acid, decylic acid, or n-decylic acid.

By "dodecanoic acid" is meant a C12 carboxylic acid having the general formula $CH_3CH_2CH_2CH_2CH_2CH_2CH_2CH_2CH_2CH_2CH_2$—COOH, optionally referred to as n-dodecanoic acid, dodecylic acid, dodecoic acid, laurostearic acid, vulvic acid, 1-undecanecarboxylic acid, or duodecylic acid.

Optionally, the composition comprises one carboxylic acid selected from butanoic acid, hexanoic acid, octanoic acid, decanoic acid, and dodecanoic acid. Further optionally, the composition comprises at least two carboxylic acids, each carboxylic acid independently selected from butanoic acid, hexanoic acid, octanoic acid, decanoic acid, and dodecanoic acid. Still further optionally, the composition comprises two carboxylic acids, each carboxylic acid independently selected from butanoic acid, hexanoic acid, octanoic acid, decanoic acid, and dodecanoic acid. Still further optionally, the composition comprises at least three carboxylic acids, each carboxylic acid independently selected from butanoic acid, hexanoic acid, octanoic acid, decanoic acid, and dodecanoic acid. Still further optionally, the composition comprises three carboxylic acids, each carboxylic acid independently selected from butanoic acid, hexanoic acid, octanoic acid, decanoic acid, and dodecanoic acid. Still further optionally, the composition comprises four carboxylic acids, each carboxylic acid independently selected from butanoic acid, hexanoic acid, octanoic acid, decanoic acid, and dodecanoic acid.

Optionally, the or each carboxylic acid is a salt of the carboxylic acid. Further optionally, the or each carboxylic acid is a potassium or sodium salt of the carboxylic acid. Still further optionally, the or each carboxylic acid is a sodium salt of the carboxylic acid.

Optionally, the composition comprises butanoic acid. Further optionally, the composition comprises 10-100% (v/v) butanoic acid. Still further optionally, the composition comprises 20-100% (v/v) butanoic acid. Still further optionally, the composition comprises 40-100% (v/v) butanoic acid. Still further optionally, the composition comprises 60-100% (v/v) butanoic acid. Still further optionally, the composition comprises 80-100% (v/v) butanoic acid.

Optionally or additionally, the composition comprises hexanoic acid. Further optionally, the composition comprises 5-100% (v/v) hexanoic acid. Still further optionally, the composition comprises 10-100% (v/v) hexanoic acid. Still further optionally, the composition comprises 20-100% (v/v) hexanoic acid. Still further optionally, the composition comprises 40-100% (v/v) hexanoic acid. Still further optionally, the composition comprises 60-100% (v/v) hexanoic acid. Still further optionally, the composition comprises 80-100% (v/v) hexanoic acid.

Optionally, the composition comprises octanoic acid. Further optionally, the composition comprises 5-100% (v/v) octanoic acid. Still further optionally, the composition comprises 5-80% (v/v) octanoic acid. Still further optionally, the composition comprises 5-60% (v/v) octanoic acid. Still further optionally, the composition comprises 5-40% (v/v) octanoic acid. Still further optionally, the composition comprises 5-30% (v/v) octanoic acid. Still further optionally, the composition comprises 5-20% (v/v) octanoic acid. Still further optionally, the composition comprises 5-10% (v/v) octanoic acid.

Optionally, the composition comprises decanoic acid. Further optionally, the composition comprises 10-100% (v/v) decanoic acid. Still further optionally, the composition comprises 10-80% (v/v) decanoic acid. Still further optionally, the composition comprises 10-60% (v/v) decanoic acid. Still further optionally, the composition comprises 10-40% (v/v) decanoic acid. Still further optionally, the composition comprises 10-30% (v/v) decanoic acid. Still further optionally, the composition comprises 10-20% (v/v) decanoic acid.

Optionally, the composition comprises dodecanoic acid. Further optionally, the composition comprises 10-100% (v/v) dodecanoic acid. Still further optionally, the composition comprises 20-100% (v/v) dodecanoic acid. Still further optionally, the composition comprises 40-100% (v/v) dodecanoic acid. Still further optionally, the composition comprises 60-100% (v/v) dodecanoic acid. Still further optionally, the composition comprises 80-100% (v/v) dodecanoic acid.

Optionally, the composition comprises 100% (v/v) butanoic acid.

Alternatively, the composition comprises butanoic acid and octanoic acid.

Optionally, the composition comprises 80% (v/v) butanoic acid and octanoic acid. Further optionally, the composition comprises 80% (v/v) butanoic acid and 10% (v/v) octanoic acid.

Optionally, the composition comprises 80% (v/v) butanoic acid, 10% (v/v) octanoic acid, and decanoic acid. Further optionally, the composition comprises 80% (v/v) butanoic acid, 10% (v/v) octanoic acid, and 10% (v/v) decanoic acid.

Optionally, the composition comprises 60% (v/v) butanoic acid and octanoic acid. Further optionally, the composition comprises 60% (v/v) butanoic acid and 20% (v/v) octanoic acid.

Optionally, the composition comprises 60% (v/v) butanoic acid, 20% (v/v) octanoic acid, and decanoic acid. Further optionally, the composition comprises 60% (v/v) butanoic acid, 20% (v/v) octanoic acid, and 20% (v/v) decanoic acid.

Optionally, the composition comprises 40% (v/v) butanoic acid and octanoic acid. Further optionally, the composition comprises 40% (v/v) butanoic acid and 30% (v/v) octanoic acid.

Optionally, the composition comprises 40% (v/v) butanoic acid, 30% (v/v) octanoic acid, and decanoic acid. Further optionally, the composition comprises 40% (v/v) butanoic acid, 30% (v/v) octanoic acid, and 30% (v/v) decanoic acid.

Optionally, the composition comprises 20% (v/v) butanoic acid and octanoic acid. Further optionally, the composition comprises 20% (v/v) butanoic acid and 40% (v/v) octanoic acid.

Optionally, the composition comprises 20% (v/v) butanoic acid, 40% (v/v) octanoic acid, and decanoic acid. Further optionally, the composition comprises 20% (v/v) butanoic acid, 40% (v/v) octanoic acid, and 40% (v/v) decanoic acid.

Alternatively, the composition comprises butanoic acid and decanoic acid.

Optionally, the composition comprises 80% (v/v) butanoic acid and decanoic acid. Further optionally, the composition comprises 80% (v/v) butanoic acid and 10% (v/v) decanoic acid.

Optionally, the composition comprises 80% (v/v) butanoic acid, 10% (v/v) decanoic acid, and octanoic acid.

Optionally, the composition comprises 60% (v/v) butanoic acid and decanoic acid. Further optionally, the composition comprises 60% (v/v) butanoic acid and 20% (v/v) decanoic acid.

Optionally, the composition comprises 60% (v/v) butanoic acid, 20% (v/v) decanoic acid, and octanoic acid.

Optionally, the composition comprises 40% (v/v) butanoic acid and decanoic acid. Further optionally, the composition comprises 40% (v/v) butanoic acid and 30% (v/v) decanoic acid.

Optionally, the composition comprises 40% (v/v) butanoic acid, 30% (v/v) decanoic acid, and octanoic acid.

Optionally, the composition comprises 20% (v/v) butanoic acid and decanoic acid. Further optionally, the composition comprises 20% (v/v) butanoic acid and 40% (v/v) decanoic acid.

Optionally, the composition comprises 20% (v/v) butanoic acid, 40% (v/v) decanoic acid, and octanoic acid.

Alternatively, the composition comprises 100% (v/v) octanoic acid.

Alternatively, the composition comprises octanoic acid and decanoic acid.

Optionally, the composition comprises 40% (v/v) octanoic acid and decanoic acid. Further optionally, the composition comprises 40% (v/v) octanoic acid and 40% (v/v) decanoic acid.

Optionally, the composition comprises 40% (v/v) octanoic acid, 40% (v/v) decanoic acid, and butanoic acid.

Optionally, the composition comprises 30% (v/v) octanoic acid and decanoic acid. Further optionally, the composition comprises 30% (v/v) octanoic acid and 30% (v/v) decanoic acid.

Optionally, the composition comprises 30% (v/v) octanoic acid, 30% (v/v) decanoic acid, and butanoic acid.

Optionally, the composition comprises 20% (v/v) octanoic acid and decanoic acid. Further optionally, the composition comprises 20% (v/v) octanoic acid and 20% (v/v) decanoic acid.

Optionally, the composition comprises 20% (v/v) octanoic acid, 20% (v/v) decanoic acid, and butanoic acid.

Optionally, the composition comprises 10% (v/v) octanoic acid and decanoic acid. Further optionally, the composition comprises 10% (v/v) octanoic acid and 10% (v/v) decanoic acid.

Optionally, the composition comprises 10% (v/v) octanoic acid, 10% (v/v) decanoic acid, and butanoic acid.

Alternatively, the composition comprises 100% (v/v) decanoic acid.

Alternatively, the composition comprises 100% (v/v) dodecanoic acid.

Optionally, the composition is a solution comprising the at least one carboxylic acid. Further optionally, the composition is an aqueous solution comprising the at least one carboxylic acid. Still further optionally, the composition is a balanced salt aqueous solution comprising the at least one carboxylic acid. Still further optionally, the composition is a balanced salt aqueous solution comprising the at least one carboxylic acid and having a physiological pH and isotonic salt concentration. Still further optionally, the composition is a balanced salt aqueous solution comprising the at least one carboxylic acid and having a physiological pH of 7.0-7.4 and isotonic salt concentration of 308 mOsm/L.

Optionally, the composition has a carboxylic acid concentration of 50-200 mM. Further optionally, the composition has a carboxylic acid concentration of 100-200 mM. Further optionally, the composition has a carboxylic acid concentration of 200 mM.

EXAMPLES

Embodiments of the present invention will now be described with reference to the following non-limiting examples.

Materials & Methods

Carboxylic Acids

Carboxylic acids were obtained from David Garnett of Pathway Intermediates Ltd or from Sigma-Aldrich Co. LLC; and compositions were prepared in a Class II cabinet at room temperature in Hank's Balanced Salt Solution (Thermo Fisher Scientific Inc.) or ethanol by vortexing strongly to emulsify at a stock concentration of 1M. Stock concentrations were diluted to working concentrations e.g. of 50-200 nM by serial dilution using Minimum Essential Medium (MEM) cell culture medium (Thermo Fisher Scientific Inc.) containing 2 mM L-Glutamine (Gibco Life Technologies Ltd.), and 100 µg/500 ml gentamycin (Lonza Group Ltd.).

Cell Culture

MARC145 cells were obtained from the Centre of Cell Cultures, Istituto Zooprofilattico Sperimentale Brescia, Italy and were maintained in Minimum Essential Medium (MEM) cell culture medium (Thermo Fisher Scientific Inc.) containing 2 mM L-Glutamine (Gibco Life Technologies Ltd.), 10% foetal calf serum (PAN-Biotech GmbH), and 100 µg/500 ml gentamycin (Lonza Group Ltd.).

MDBK cells were obtained from ECACC and were maintained in Minimum Essential Medium (MEM) cell culture medium (Thermo Fisher Scientific Inc.) containing 2 mM L-Glutamine (Gibco Life Technologies Ltd.), 10% foetal calf serum (PAN-Biotech GmbH), 100 µg/500 ml gentamycin (Lonza Group Ltd.), and 1% essential non essential amino acids (Sigma-Aldrich Co. LLC.).

PK15A cells were obtained from the European Union Reference Laboratory for Classical Swine Fever. These cells are a porcine circovirus-free sub-clone of PK15, an adherent porcine kidney epithelial cell line (ATCC CCL-33) (Dulac G C, Afshar A. Porcine circovirus antigens in PK-15 cell line (ATCC CCL-33) and evidence of antibodies to circovirus in Canadian pigs. Can. J. Vet. Res. 53: 431-433, 1989). The cells were maintained in Minimum Essential Medium (MEM) cell culture medium (Thermo Fisher Scientific Inc.) containing 2 mM L-Glutamine (Gibco Life Technologies Ltd.), 10% foetal calf serum (PAN-Biotech GmbH), and 100 µg/500 ml gentamycin (Lonza Group Ltd.).

MA104 cells were obtained from ECACC and were maintained in Minimum Essential Medium (MEM) cell culture medium (Thermo Fisher Scientific Inc.) containing 2 mM L-Glutamine (Gibco Life Technologies Ltd.), 10% foetal calf serum (PAN-Biotech GmbH), and 100 µg/500 ml gentamycin (Lonza Group Ltd.).

A primary pig kidney (PPK) cell line was sourced from a kidney of a sacrificed piglet from the Agri-Food and Biosciences Institute (AFBI Hillsborough, UK). The kidney tissue was trypsinised to create a PPK cell line, which was maintained in Minimum Essential Medium (MEM) cell culture medium (Thermo Fisher Scientific Inc.) containing 2 mM L-Glutamine (Gibco Life Technologies Ltd.), 10% foetal calf serum (PAN-Biotech GmbH), and 100 µg/500 ml gentamycin (Lonza Group Ltd.).

In general, cells were seeded as at a density of 0.313e4-5.000e4 cells per 1 ml of cell suspension in growth medium, dispensed in to a SPL 24-Well Cell Culture Plate (SPL Life Sciences Co., Ltd.) in replicates of 3, each containing Academy Circular Cover Slips (Academy Science) and incubated overnight at 37° C. at 5% $CO_2$. The growth medium was removed and replaced with 1 ml of Minimum Essential Medium (MEM) cell culture medium (Thermo Fisher Scientific Inc.) containing 2 mM L-Glutamine (Gibco Life Technologies Ltd.), and 100 µg/500 ml gentamycin (Lonza Group Ltd.) for treatment.

Viruses

Viruses were obtained from the following sources:

PRRS from Ingelvac PRRS® MLV vaccine (Boehringer Ingelheim).

Porcine circovirus type 2 (PCV2) was sourced from Prof. John Ellis, Canada; from a field sample import 1010 P41 taken from a pig with post-weaning multisystemic wasting syndrome. The virus is a small ssDNA non-enveloped virus, about 17 nm in diameter with a monopartite, circular, ssDNA genome of approximately 1.7-1.8 kb, family Circoviridae) (Meehan, B. M., McNeilly, F., Todd, D., Kennedy, S., Jewhurst, V. A., Ellis, J. A., Hassard, L. E., Clark, E. G., Haines, D. M. and Allan, G. M. Characterization of novel circovirus DNAs associated with wasting syndromes in pigs; J. Gen. Virol. 79 (Pt 9), 2171-2179 (1998), GenBank accession number AF055392.

Porcine rotavirus was PROSYSTEM® ROTA PORCINE ROTAVIRUS VACCINE (Merck Animal Health).

Porcine enterovirus T80 Pool 8 was sourced from Weybridge, UK. This porcine enterovirus is now reclassified as porcine teschovirus 2, ssRNA positive-strand viruses, family Picornavirales, genus Teschovirus (Kaku, Y., Sarai, A. and Murakami, Y. Genetic reclassification of porcine enteroviruses; J. Gen. Virol. 82 (PT 2), 417-424 (2001)). The virus is non-enveloped, spherical, approximately 30 nm in diameter with a monopartite, linear, ssRNA(+) genome of 7.1 kb, polyadenylated, composed of a single ORF encoding a polyprotein.

Porcine adenovirus Wat52 Pool 1 was sourced from a faeces sample taken on a farm in Northern Ireland. The virus has a non-enveloped capsid with a diameter of approximately 90 nm and a non-segmented, linear double-stranded DNA of 35-36 kb (GenBank accession number AF289262, Nagy, M., Nagy, E. and Tuboly, T. The complete nucleotide sequence of porcine adenovirus serotype 5, J. Gen. Virol. 82 (Pt 3), 525-529 (2001)).

Porcine parvovirus 1005 Pool 8 N96 4713 was sourced from Dr. T Clarke, Saskatoon, Canada. The virus is a small non-enveloped virus with a capsid of 18-26 nm in diameter and a linear, ssDNA genome of about 4 to 6 kb in size. The virus belongs to the family Parvoviridae, genus Protoparvovirus (GenBank accession number NC_001718; Hueffer K, Parrish C R. Parvovirus host range, cell tropism and evolution. Curr Opin Microbiol. 2003 August; 6(4):392-8. Review).

Infectious bovine rhinotracheitis virus (IBRV) (Bovine Herpes 1) IBR WP.1 was used, derived from a working pool M3 from Dr Lucas Weybridge, North American strain Colorado. The virus belongs to the order Herpesvirales, family Herpesviridae, subfamily Alphaherpesvirinae, genus Varicellovirus. The virus has an enveloped, spherical to pleomorphic capsid, 150-200 nm in diameter and a monopartite, linear, dsDNA genome of about 125 kb (GenBank accession number KU198480; Curtis R A, Van Dreumel A A, Ditchfield J. Infectious bovine rhinotracheitis—clinical, pathological, and virological aspects. Can Vet J. 1966 August; 7(8):161-8. Review).

All viruses were stored at −80° C., aliquoted as stock pools and working pools under ISO9001 conditions with electronic temperature monitoring of freezers.

Treatment

Prior to treatment, the cells and coverslips were washed three times with Minimum Essential Medium (MEM) cell culture medium (Thermo Fisher Scientific Inc.) containing 2 mM L-Glutamine (Gibco Life Technologies Ltd.), and 100 µg/500 ml gentamycin (Lonza Group Ltd.). 100 µl of the virus at a titre of $10^9$ $TCID_{50}$/100 µl by the Reed-Muench method, and 100 µl of the treatment samples, were incubated for 30 mins at 37° C. at 5% $CO_2$ The reaction was stopped by adding 800 µl of Minimum Essential Medium (MEM) cell culture medium (Thermo Fisher Scientific Inc.) containing 2 mM L-Glutamine (Gibco Life Technologies Ltd.), and 100 µg/500 ml gentamycin (Lonza Group Ltd.). Each treatment/virus was titrated out, initially 100 µl of each treatment was added to 900 µls of Minimum Essential Medium (MEM) cell culture medium (Thermo Fisher Scientific Inc.) containing 2 mM L-Glutamine (Gibco Life Technologies Ltd.), and 100 µg/500 ml gentamycin (Lonza Group Ltd.) to prepare a $10^{-1}$ dilution. The $10^{-1}$ dilution was then diluted in serial dilutions down to $10^{-6}$ in the same medium 100 µl of media was then added to each appropriate well in replicates of 3 and incubated for 36 hours at 37° C. at 5% $CO_2$ Ethanol or PBS were used as control treatments. Untreated cells were used as negative controls.

Staining

After incubation, coverslips were harvested. Each slip was harvested by lifting out of the medium with forceps then rinsing and fixing by dipping sequentially into glass universal bottles of PBS, acetone, and lastly acetone. The slip was then placed cells side up in a glass Petri dish of acetone in a Class II cabinet at room temperature for 10 minutes. Coverslips were stained by immunofluorescence assay (IFA) using primary monoclonal antibody at a dilution of 1/5000 (PRRSV Monoclonal Antibody: SDOW17 from RTI, LLC; anti-bovine BHV1 (IBR/IPV) FITC conjugated Monoclonal antibody: BIO 026 from Bio-X Diagnostics S.P.R.L; Rabbit anti-rotavirus Group A antiserum from Bio-Rad Laboratories, Inc; Anti-Rotavirus antibody [A2] (ab181695) from Abcam plc; PCV2 MAB F217 2c6-H9-A2—this monoclonal antibody was produced at AFBI Veterinary Sciences Division in the model non-secreting murine myeloma NSO cell line against PCV2 strain 48285, a type 2b field isolate from France, taken from a pig with a pig with post-weaning multisystemic wasting syndrome); convalescent pig anti serum(convalescent pig serum was simply a serum pool from 5 sows from a single farm in Northern Ireland); Porcine Parvovirus (PPV) MAb IgG1 Isotype from VMRD, Inc.

The slips were stained for 1 hour in a humidity chamber at 37° C. at 5% $CO_2$ before rinsing in PBS. The secondary stain was applied as an polyclonal rabbit anti-mouse FITC (Dako Denmark NS); polyclonal goat anti-rabbit FITC (Nordic-MUbio BV); rabbit anti-swine FITC (Nordic-MUbio BV) at 1/100 dilution, as appropriate.

The secondary stain was left again for 1 hour in the same humidity chamber. The slips were then rinsed in PBS and mounted onto mounting medium cell side down onto a microscope slide with dull edges and plain end (VWR International Ltd). The microscope slides were read using IF microscopes (Leica Microsystems), and scored in detail from 3+ to −ve by independent analysts Paula Lagan, Scientific Officer and Karen McKay, Assistant Scientific Officer from Porcine Virology R+D laboratory AFBI VSD, and then summarised as a basic score.

| | |
|---|---|
| 3+ | Good bright staining in all fields where >50% cells are stained |
| 2+ | Per field of view ≥20% cells stained |
| 1+ | At least one well stained cell and preferable in more than one field of view. |
| +/− | Some fluorescence but unsure if positive may suggest presence of virus |

Example 1

Virucidal Affects of Compositions of the Present Invention on Porcine Respiratory and Reproductive Syndrome Virus (PRRSV)

Test compositions were prepared and treated as described above and as follows:

A. Sodium butyrate.

B. Sodium butyrate, capric and caprylic acid as a ratio of 80:10:10.

C. Sodium butyrate, capric and caprylic acid as a ratio of 60:20:20.

Issues with the test 3 as cells were absent from some wells or other wells were difficult to read. Test 4 minimum reduction in titre of 3 logs with both mixes and 80:10:10 reductions in titre were 4.5 logs.

The enveloped-RNA PRRSV was unaffected at a concentration of 100 mM. Raising the concentration to 200 mM of butyric acid gives a 3.5 $\log_{10}$ reduction in titre while raising the concentration of the butyric acid mix eliminates infectious virus totally. There is no significant difference between the (80:10:10) and the (60:20:20) mixes.

Example 2

Virucidal affects of compositions of the present invention on infectious bovine rhinotracheitis virus (IBRV) Test compositions were prepared and treated as described above and as follows:

A. Sodium Butyrate

B. Sodium Butyrate, Capric and Caprylic Acid as a ratio of 80:10:10

TABLE 1

Results; PRRS results for the treatment A and B

| | Test | | | | | | | | | | | | | | | |
|---|---|---|---|---|---|---|---|---|---|---|---|---|---|---|---|---|
| | 1 | | 2 | | 1 | | 2 | | 1 | | 2 | | 1 | | 2 | |
| | Treatment A | | Treatment B | | Treatment A | | Treatment B | | Virus | | Virus | | Virus | | Virus | |
| Dilution | 100 mM | | 100 mM | | 200 mM | | 200 mM | | and PBS | | and PBS | | and ethanol | | and ethanol | |
| $10^{-1}$ | + | + | + | + | + | + | − | − | + | + | + | + | + | + | + | + |
| $10^{-2}$ | + | + | + | + | + | + | − | − | + | + | + | + | + | + | + | + |
| $10^{-3}$ | + | + | − | + | + | + | − | − | + | + | + | + | + | + | + | + |
| $10^{-4}$ | + | + | − | − | + | + | − | − | + | + | + | + | + | + | + | + |
| $10^{-5}$ | + | + | − | − | + | + | − | − | + | + | + | + | + | + | + | + |
| $10^{-6}$ | + | + | − | − | + | + | − | − | + | + | + | + | + | + | − | + |

Test 1: no reduction in titre.

Test 2: Significant reductions in titre at $10^{-2}$ with treatment A as only occasional cell at the $10^{-2}$ dilution. No positive staining with the treatment B.

TABLE 2

PRRS results for the treatment B and C

| | Test | | | | | | | | | | | |
|---|---|---|---|---|---|---|---|---|---|---|---|---|
| | 3 | | 4 | | 3 | | 4 | | 3 | | 4 | |
| | Treatment B | | Treatment B | | Treatment C | | Treatment C | | Virus and | | Virus and | |
| Dilution | 80:10:10 | | 80:10:10 | | 60:20:20 | | 60:20:20 | | ethanol | | ethanol | |
| $10^{-1}$ | + | + | + | + | + | − | + | + | + | + | + | + |
| $10^{-2}$ | + | + | − | − | − | − | + | + | + | + | + | + |
| $10^{-3}$ | + | − | + | − | − | − | + | + | + | + | + | + |
| $10^{-4}$ | − | − | − | − | − | − | − | − | + | + | + | + |
| $10^{-5}$ | − | − | − | − | − | − | − | − | + | + | + | + |
| $10^{-6}$ | − | − | − | − | − | − | − | − | + | + | + | + |

TABLE 3

IBRV results

| | Test | | | | | | | | | |
|---|---|---|---|---|---|---|---|---|---|---|
| | Treatment A 100 mM | | Treatment B 100 mM | | Treatment B 200 mM | | Virus and PBS | | Virus and ethanol | |
| Dilution | 1 | 2 | 1 | 2 | 1 | 2 | 1 | 2 | 1 | 2 |
| $10^{-1}$ | − | − | + | + | − | − | + | + | + | + |
| $10^{-2}$ | − | − | + | + | − | − | + | + | + | + |
| $10^{-3}$ | − | − | − | − | − | − | + | + | + | + |
| $10^{-4}$ | − | − | − | − | − | − | + | + | + | + |
| $10^{-5}$ | − | − | − | − | − | − | + | + | + | + |
| $10^{-6}$ | − | − | − | − | − | − | + | + | + | + |

For the enveloped-DNA IBRV; a 4 $\log_{10}$ reduction in titre observed using a 100 mM butyric acid and complete inactivation using the B:C:C mix (80:10:10).

Example 3

Virucidal affects of compositions of the present invention on porcine circovirus (PCV2) Virus in PK15A cells.

Test compositions were prepared and treated as described above and as follows:

A. Sodium Butyrate

B. Sodium Butyrate, Capric and Caprylic Acid as a ratio of 80:10:10

TABLE 4

PCV2 results

| | Test | | | | | | | | | |
|---|---|---|---|---|---|---|---|---|---|---|
| | Treatment A 100 mM | | Treatment B 100 mM | | Treatment B 200 mM | | Virus and PBS | | Virus and ethanol | |
| Dilution | 1 | 2 | 1 | 2 | 1 | 2 | 1 | 2 | 1 | 2 |
| $10^{-1}$ | + | + | + | + | + | + | + | + | + | + |
| $10^{-2}$ | + | + | + | + | + | + | + | + | + | + |
| $10^{-3}$ | + | + | + | + | + | + | + | + | + | + |
| $10^{-4}$ | + | + | + | + | + | + | + | + | + | + |
| $10^{-5}$ | + | + | − | − | + | + | − | − | + | + |
| $10^{-6}$ | + | + | − | − | + | + | − | − | + | + |

No reduction in titre was seen. The non-enveloped DNA PCV2 is not susceptible to treatment with butyric acid or the mixes at either 100 or 200 mM.

Example 4

Virucidal Affects of Compositions of the Present Invention on Porcine Rotavirus in MA104 Cells.

Test compositions were prepared and treated as described above and as follows:

A. Sodium Butyrate

B. Sodium Butyrate, Capric and Caprylic Acid as a ratio of 80:10:10

C. Sodium Butyrate Capric and Caprylic Acid 60:20:20

TABLE 5

Porcine rotavirus results

| Expt | Date | FA conc (mM) | Incubation (mins) | DMSO | Titre Butyric | Titre 60:20:20 | Titre 80:10:10 | Titre ETOH | Titre PBS |
|---|---|---|---|---|---|---|---|---|---|
| 1 | 3 Nov. 2009 | 100 | 30 | ✓ | −4 | Not done | −2* | −4 | −4 |
| 2 | 10 Nov. 2009 | 200 | 30 | ✓ | −2 | Not done | −2* | −4 | −4 |
| 3 | 5 Mar. 2010 | 200 | 30 | ✓ | Not done | −3 | −3 | −3 | Not done |
| 4 | 12 Mar. 2010 | 200 | 30 | ✓ | Not done | −4 | −4 | −4 | Not done |

TABLE 5-continued

Porcine rotavirus results

| Expt | Date | FA conc (mM) | Incubation (mins) | DMSO | Titre Butyric | Titre 60:20:20 | Titre 80:10:10 | Titre ETOH | Titre PBS |
|---|---|---|---|---|---|---|---|---|---|
| 5a | 19 Mar. 2010 | 200 | 30 | ✓ | Not done | −4 | −4 | −4 | Not done |
| 5b | 19 Mar. 2010 | 200 | 60 | ✓ | Not done | −4 | −4 | −4 | Not done |
| 6 | 13 Apr. 2010 | 200 | 30 | X | Not done | −1 | −2 | −4 | Not done |
| 7 | 1 Jun. 2010 | 200 | 30 | X | | No staining - some problem | | | |
| 8 | 21 Jun. 2010 | 200 | ? | X | Not done | −1 | −1 | −4 | Not done |

The non-enveloped RNA porcine rotavirus was affected by butyric acid mix at 100 mM concentration (2 log 10 reduction in titre). Increasing this concentration to 200 mM does not improve the effect, but increasing the butyric acid alone to this concentration achieves the same reduction in titre (2 log 10 reduction).

Example 5

Virucidal Affects of Compositions of the Present Invention on Porcine Enterovirus, Adenovirus and Parvovirus in Primary Pig Kidney Cells.

Test compositions were prepared and treated as described above and as follows:
B. Sodium Butyrate, Capric and Caprylic Acid as a ratio of 80:10:10
C. Sodium Butyrate Capric and Caprylic Acid 60:20:20

TABLE 6

Adenovirus results

| | Test | | | | | | | |
|---|---|---|---|---|---|---|---|---|
| Dilution | 1 Treatment A 200 mM | 2 Treatment B 200 mM * | 1 Treatment A 200 mM | 2 Treatment B 200 mM | 2 Virus and ethanol | | 1 Virus and ethanol | |
| $10^{-1}$ | + | + | + | + | + | + | + | + |
| $10^{-2}$ | + | + | + | + | + | + | + | + |
| $10^{-3}$ | + | + | + | + | + | + | + | + |
| $10^{-4}$ | − | − | − | − | − | − | − | − |
| $10^{-5}$ | − | − | − | − | − | − | − | − |
| $10^{-6}$ | − | − | − | − | − | − | − | − |

Test 2: Treatment B no results as too difficult to score. No significant effect. The non-enveloped porcine adenovirus was not susceptible to treatment with either of the butyric acid mixes (80:10:10) or (60:20:20).

TABLE 7

Enterovirus results

| | Test | | |
|---|---|---|---|
| Dilution | 1 Treatment A 200 mM | 1 Treatment B 200 mM | 1 Virus and ethanol |
| $10^{-1}$ | + | + | + + + + |
| $10^{-2}$ | + | + | + + + + |
| $10^{-3}$ | + | + | + + + + |
| $10^{-4}$ | + | + | + + + + |

TABLE 7-continued

Enterovirus results

| | Test | | |
|---|---|---|---|
| Dilution | 1 Treatment A 200 mM | 1 Treatment B 200 mM | 1 Virus and ethanol |
| $10^{-5}$ | + | + | + + + + |
| $10^{-6}$ | − | − | − − + + |

No significant effect was seen. The non-enveloped RNA porcine enterovirus was not susceptible to treatment with either of the butyric acid mixes (80:10:10) or (60:20:20).

TABLE 8

Parvovirus virus results

| | Test | | |
|---|---|---|---|
| Dilution | 1 Treatment A 200 mM | 1 Treatment B 100 mM | 1 Virus and ethanol |
| $10^{-1}$ | + + | + + | + + |
| $10^{-2}$ | + + | + + | + + |
| $10^{-3}$ | + + | + + | + + |
| $10^{-4}$ | + + | + + | + + |
| $10^{-5}$ | + + | + + | + + |
| $10^{-6}$ | + + | + + | + + |

No effect was seen. The non-enveloped PPV was not susceptible to treatment with either of the butyric acid mixes (80:10:10) or (60:20:20).

Example 6

Virucidal Affects of Compositions of the Present Invention on Porcine Rotavirus in Primary Pig Kidney Cells.

Test compositions were prepared and treated as described above and as follows; 1 ml of 1M compositions of the present invention were added to 4 mls of medium to equate to a total carboxylic acid concentration of 200 mM, and the following results were obtained:

TABLE 9

Porcine rotavirus results

| Composition | Ratio | Result Replicate 1 | Result Replicate 2 | Result Replicate 3 |
|---|---|---|---|---|
| Butyric Acid C4 (1M) | C4 100 | | –ve | –ve |
| Butyric Acid C4 (800 mM): | C4 80: | –ve | –ve | |
| Octanonic Acid/Caprylic C8 (100 mM): | C8 10: | | | |
| Decanoic Acid/Capric C10 (100 mM) | C10 10 | | | |
| Butyric Acid C4 (600 mM): | C4 60: | –ve | –ve | |
| Octanonic Acid/Caprylic C8 (200 mM): | C8 20: | | | |
| Decanoic Acid/Capric C10 200 mM | C10 20 | | | |
| Butyric Acid C4 (400 mM): | C4 40: | –1 | –1 | |
| Octanonic Acid/Caprylic C8 (300 mM): | C8 30: | | | |
| Decanoic Acid/Capric C10 (300 mM) | C10 30 | | | |
| Butyric Acid C4 (200 mM: | C4 20: | | –1 | –1 |
| Octanonic Acid/Caprylic C8 (400 mM): | C8 40: | | | |
| Decanoic Acid/Capric C10 (400 mM) | C10 40 | | | |
| Octanonic Acid/Caprylic C8 (1M) | C8 100 | | –2 | –1 |
| Decanoic Acid/Capric C10 (1M) | C10 100 | | –1 | –ve |
| Dodecanoic acid/Lauric C12 (1M) | C12 100 | NA | –ve | –1 |
| PBS | | –4 | –5 | –5 |
| ETHANOL | | –4 | –4 | –5 |
| Untreated | | –ve | –ve | –ve |

The present invention provides a composition for use in treating rotavirus infection by providing compositions having an anti-viral effect on candidate rotavirus group A live attenuated pig vaccines and capable of reducing rotavirus titre, a non-enveloped RNA virus. This effect was enhanced by modification of the compositions, resulting in a >2 $\log_{10}$ reduction in rotavirus infectious titre following in-vitro culture. Increasing the concentration of the compositions did not improve the effect, but increasing the concentration of specific carboxylic acids within the compositions achieved the same reduction in titre (2 $\log_{10}$ reduction). This anti-viral effect on rotavirus has significant potential for future study for use in control of neonatal enteritis in production animals and human health.

We claim:

1. A method of treating a Reoviridae viral infection in a subject, the method comprising administering to said subject a composition wherein the composition comprises:
   80% (v/v) butanoic acid and 10% (v/v) octanoic acid;
   80% (v/v) butanoic acid, 10% (v/v) octanoic acid, and 10% (v/v) decanoic acid;
   60% (v/v) butanoic acid, 20% (v/v) octanoic acid, and 20% (v/v) decanoic acid;
   40% (v/v) butanoic acid, 30% (v/v) octanoic acid, and 30% (v/v) decanoic acid;
   20% (v/v) butanoic acid, 40% (v/v) octanoic acid, and 40% (v/v) decanoic acid;
   80% (v/v) butanoic acid and 10% (v/v) decanoic acid;
   60% (v/v) butanoic acid and 20% (v/v) decanoic acid;
   40% (v/v) butanoic acid and 30% (v/v) decanoic acid; or
   20% (v/v) butanoic acid and 40% (v/v) decanoic acid.

2. The method of claim 1, wherein the composition comprises 80% (v/v) butanoic acid, 10% (v/v) octanoic acid, and 10% (v/v) decanoic acid.

3. The method of claim 1, wherein the composition comprises 60% (v/v) butanoic acid, 20% (v/v) octanoic acid, and 20% (v/v) decanoic acid.

4. The method of claim 1, wherein the composition comprises 40% (v/v) butanoic acid, 30% (v/v) octanoic acid, and 30% (v/v) decanoic acid.

5. The method of claim 1, wherein the composition comprises 20% (v/v) butanoic acid, 40% (v/v) octanoic acid, and 40% (v/v) decanoic acid.

6. The method of claim 1, wherein the composition comprises 80% (v/v) butanoic acid and 10% (v/v) decanoic acid.

7. The method of claim 1, wherein the composition comprises 60% (v/v) butanoic acid and 20% (v/v) decanoic acid.

8. The method of claim 1, wherein the composition comprises 40% (v/v) butanoic acid and 30% (v/v) decanoic acid.

9. The method of claim 1, wherein the composition comprises 20% (v/v) butanoic acid and 40% (v/v) decanoic acid.

10. A method of treating a Reoviridae viral infection in a subject, the method comprising administering to said subject a composition, wherein the composition is an aqueous acid solution wherein the acid consists of butanoic acid and at least one carboxylic acid selected from hexanoic acid, octanoic acid, decanoic acid, and dodecanoic acid.

11. A method of treating a Reoviridae viral infection in a subject, the method comprising administering to said subject a composition, wherein the composition is an aqueous acid solution wherein the acid consists of 20 to 80% (v/v) butanoic acid, 5-30% (v/v) octanoic acid and 10-40% (v/v) decanoic acid.

12. The method of claim 10, wherein the composition has a carboxylic acid concentration of 50-200 mM.

13. The method of claim 1, wherein the composition comprises 80% (v/v) butanoic acid and 10% (v/v) octanoic acid.

* * * * *